(12) United States Patent
Koch et al.

(10) Patent No.: US 7,702,202 B2
(45) Date of Patent: Apr. 20, 2010

(54) OPTICAL MICRORESONATOR

(75) Inventors: Barry J. Koch, Woodbury, MN (US);
Terry L. Smith, Roseville, MN (US);
Yasha Yi, Woodbury, MN (US);
Chunmei Guo, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/565,935

(22) Filed: Dec. 1, 2006

(65) Prior Publication Data

US 2008/0131049 A1    Jun. 5, 2008

(51) Int. Cl.
G02B 6/26    (2006.01)
G02B 6/42    (2006.01)

(52) U.S. Cl. .......................... 385/50; 385/129; 385/15; 385/27; 385/31; 385/32; 385/35

(58) Field of Classification Search ........................ None
See application file for complete search history.

(56) References Cited

U.S. PATENT DOCUMENTS

| | | | |
|---|---|---|---|
| 4,185,257 A | 1/1980 | Nakajima | |
| 4,775,214 A | 10/1988 | Johnson | |
| 5,398,256 A | 3/1995 | Hohimer et al. | |
| 5,420,880 A | 5/1995 | Tabatabaie et al. | |
| 5,537,432 A | 7/1996 | Mehuys et al. | |
| 5,651,018 A | 7/1997 | Mehuys et al. | |
| 5,748,663 A | 5/1998 | Chenausky | |
| 5,910,963 A | 6/1999 | Simon | |
| 6,009,115 A | 12/1999 | Ho | |
| 6,286,262 B1 | 9/2001 | Prevot et al. | |
| 6,490,039 B2 | 12/2002 | Maleki et al. | |
| 6,515,749 B2 * | 2/2003 | Pipino | 356/440 |
| 6,580,851 B1 | 6/2003 | Vahala et al. | |
| 6,583,399 B1 | 6/2003 | Hunziker et al. | |
| 6,608,716 B1 | 8/2003 | Armstrong et al. | |
| 6,657,731 B2 | 12/2003 | Tapalian et al. | |
| 6,661,950 B1 | 12/2003 | Strecker | |

(Continued)

FOREIGN PATENT DOCUMENTS

WO    WO 98/53535    11/1998

(Continued)

OTHER PUBLICATIONS

U.S. Appl. No. 11/277,769, filed Mar. 29, 2006, entitled "Coupling Light Into Microresonators."

(Continued)

*Primary Examiner*—Uyen-Chau N Le
*Assistant Examiner*—Chad H Smith
(74) *Attorney, Agent, or Firm*—Robert S. Moshrefzadeh

(57) ABSTRACT

An optical device and a sensor system incorporating same are disclosed. The optical device includes a microresonator that has a core with input and output ports. The output port is different than the input port. The optical device further includes first and second optical waveguides. Each optical waveguide has a core with input and output faces. The output face of the core of the first optical waveguide physically contacts the input port of the core of the microresonator. The input face of the core of the second optical waveguide physically contacts the output port of the core of the microresonator.

37 Claims, 9 Drawing Sheets

U.S. PATENT DOCUMENTS

| | | |
|---|---|---|
| 6,680,962 B2 | 1/2004 | Liu et al. |
| 6,711,200 B1 | 3/2004 | Scherer et al. |
| 6,751,368 B2 | 6/2004 | Lim et al. |
| 6,772,480 B2 | 8/2004 | Prevot et al. |
| 6,781,690 B2 | 8/2004 | Armstrong et al. |
| 6,795,481 B2 | 9/2004 | Maleki et al. |
| 6,876,796 B2 | 4/2005 | Garito et al. |
| 6,888,987 B2* | 5/2005 | Sercel et al. .................. 385/39 |
| 6,901,101 B2 | 5/2005 | Frick |
| 6,947,632 B2 | 9/2005 | Fischer et al. |
| 7,062,131 B2 | 6/2006 | Ilchenko |
| 7,085,452 B1 | 8/2006 | Lin et al. |
| 7,271,379 B2* | 9/2007 | Fan et al. ..................... 250/216 |
| 7,292,112 B2 | 11/2007 | Oxborrow |
| 2002/0122179 A1 | 9/2002 | Pipino |
| 2003/0063426 A1 | 4/2003 | Smirnov et al. |
| 2003/0202555 A1 | 10/2003 | Liu et al. |
| 2003/0231826 A1 | 12/2003 | Boyd et al. |
| 2004/0023396 A1 | 2/2004 | Boyd et al. |
| 2004/0137478 A1 | 7/2004 | Arnold et al. |
| 2004/0247008 A1 | 12/2004 | Scheuer et al. |
| 2005/0003520 A1 | 1/2005 | Misiakos et al. |
| 2005/0013529 A1 | 1/2005 | Chiu et al. |
| 2005/0018274 A1 | 1/2005 | Halas et al. |
| 2005/0077513 A1 | 4/2005 | Fan et al. |
| 2005/0078731 A1 | 4/2005 | Fan et al. |
| 2005/0141809 A1 | 6/2005 | Gardner et al. |
| 2005/0210989 A1 | 9/2005 | Ja et al. |
| 2005/0226564 A1* | 10/2005 | Gardner et al. ................ 385/50 |
| 2005/0263679 A1 | 12/2005 | Fan et al. |
| 2005/0286602 A1 | 12/2005 | Gunn et al. |
| 2006/0062508 A1 | 3/2006 | Guo et al. |
| 2006/0170931 A1 | 8/2006 | Guo et al. |
| 2007/0001773 A1 | 1/2007 | Oxborrow |
| 2007/0147445 A1 | 6/2007 | Ishaaya et al. |

FOREIGN PATENT DOCUMENTS

| | | |
|---|---|---|
| WO | WO 01/40757 | 6/2001 |
| WO | WO 2005/116615 | 12/2005 |

OTHER PUBLICATIONS

U.S. Appl. No. 11/565,920, filed Dec. 1, 2006, entitled "Optical Sensing Device."

U.S. Appl. No. 11/565,955, filed Dec. 1, 2006 entitled "Optical Sensing Methods."

U.S. Appl. No. 11/617,923, filed Dec. 29, 2006, entitled "Optical Devices and Methods."

U.S. Appl. No. 11/616,338, filed Dec. 27, 2006, entitled "Optical Microresonator."

U.S. Appl. No. 11/617,932, filed Dec. 29, 2006, entitled "Optical Sensing Devices and Methods."

Brun et al., "Coupling nanocrystals to a high-Q silica microsphere: Entanglement in quantum dots via photon exchange," *Physical Review A*, vol. 61, pp. 032307-1-5 (2000).

Fan et al., "Coupling semiconductor nanocrystals to a fused-silica microsphere: a quantum-dot microcavity with extremely high Q factors," *Optics Letters*, vol. 25, No. 21 pp. 1600-1602 (Nov. 1, 2000).

Fano, "Effects of Configuration Interaction on Intensities and Phase Shifts," *Physical Review*, vol. 124, No. 6, pp. 1866-1878 (Dec. 15, 1961).

Götzinger et al., "Towards controlled coupling between a high-Q whispering-gallery mode and a single nanoparticle," *Appl. Phys. B*, vol. 73, pp. 825-828 (2001).

Little et al., "Second-order filtering and sensing with partially coupled traveling waves in a single resonator", *Optics Letters*, vol. 23, No. 20, pp. 1570-1572 (Oct. 15, 1998).

Soller et al., "Dynamic modifications to the plasmon resonance of a metallic nanoparticle coupled to a planar waveguide: beyond the point-dipole limit," *J. Opt. Soc. Am. B.*, vol. 19, No. 5, pp. 1195-1203 (May 2002).

Xu, et al., "Scattering-theory analysis of waveguide-resonator coupling," *Physical Review E*, vol. 62, No. 5, pp. 7389-7404 (Nov. 2000).

\* cited by examiner

OPTICAL MICRORESONATOR

FIELD OF THE INVENTION

This invention generally relates to optical devices. The invention is particularly applicable to optical devices such as optical sensors that incorporate microresonators.

BACKGROUND

Microresonators have received increasing attention in various applications such as optical switching described in, for example, U.S. Pat. No. 6,876,796; optical filtering described in, for example, U.S. Pat. No. 7,092,591; wavelength filtering described in, for example, U.S. Pat. No. 7,062,131; optical lasers described in, for example, U.S. Pat. No. 6,741,628; light depolarization described in, for example, U.S. Pat. No. 6,891,998; and chemical and biological sensing described in, for example, U.S. Pat. No. 5,744,902.

Some known microresonator constructions involve placing a glass spherical microresonator in close proximity to an optical waveguide such as an optical fiber. In such cases, optical energy can transfer between the resonator and the optical waveguide by evanescent coupling. The separation between the resonator and the optical waveguide is typically less than one micron and must be controlled with precision to provide reproducible performance. Other forms of microresonators include disk- or ring-shaped microresonators described in, for example, U.S. Pat. No. 7,095,010.

SUMMARY OF THE INVENTION

Generally, the present invention relates to optical devices. The present invention also relates to optical sensors that include one or more microresonators.

In one embodiment, an optical device includes a microresonator that has a core with input and output ports. The output port is different than the input port. The optical device further includes first and second optical waveguides. Each optical waveguide has a core with input and output faces. The output face of the core of the first optical waveguide physically contacts the input port of the core of the microresonator. The input face of the core of the second optical waveguide physically contacts the output port of the core of the microresonator.

In another embodiment, an optical device includes a microresonator that has a circular symmetry. The microresonator has a core. The optical device further includes an optical waveguide having a core. The waveguide core terminates at the core of the microresonator.

In another embodiment, an optical device includes a light source, an optical detector, and a microresonator that is capable of supporting first and second guided counter traveling optical modes. The second guided optical mode is different than the first guided optical mode. The microresonator has a core with input and output ports where the output port is different than the input port. The microresonator is capable of bonding with an analyte associated with a scattering center. The optical device further includes a first optical waveguide that has a core with an input face in optical communication with the light source and an output face in physical contact with the input port of the core of the microresonator. The optical device further includes a second optical waveguide that has a core with an input face physically contacting the output port of the core of the microresonator and an output face in optical communication with the optical detector. When the associated analyte bonds with the microresonator, the scattering center is capable of inducing an optical scattering between the first and second guided optical modes. The optical scattering results in a transfer of energy from the first guided mode to the second guided mode. The optical detector detects the transfer of energy.

In another embodiment, an optical device includes a microresonator that is capable of supporting at least two resonant optical modes. At least one of the two resonant modes is capable of propagating within the microresonator while maintaining a same electric field profile. The optical device further includes first and second optical waveguides that are capable of coupling to the microresonator by core coupling.

In another embodiment, an optical device includes a microresonator that has a core. The optical device further includes a first optical waveguide that has a core that extends from a first location on the core of the microresonator. The optical device further includes a second optical waveguide that has a core that extends from a second location on the core of the microresonator. The second location is different from the first location.

BRIEF DESCRIPTION OF DRAWINGS

The invention may be more completely understood and appreciated in consideration of the following detailed description of various embodiments of the invention in connection with the accompanying drawings, in which.

In the specification, a same reference numeral used in multiple figures refers to the same or similar elements having the same or similar properties and functionalities.

DETAILED DESCRIPTION

This invention generally relates to optical devices. The invention is particularly applicable to optical devices such as optical sensors that incorporate microresonators.

The present invention describes an optical device that includes one or more waveguides optically coupled to an optical microresonator. The performance of the disclosed embodiments is relatively insensitive to the placement of the optical waveguide(s) relative to the optical microresonator. As such, the present invention can reduce manufacturing costs since, for example, manufacturing errors and/or limitations in placing the optical waveguide(s) in optical proximity with the optical microresonator are less likely to result in a substantial change in the optical coupling.

Figure 1:
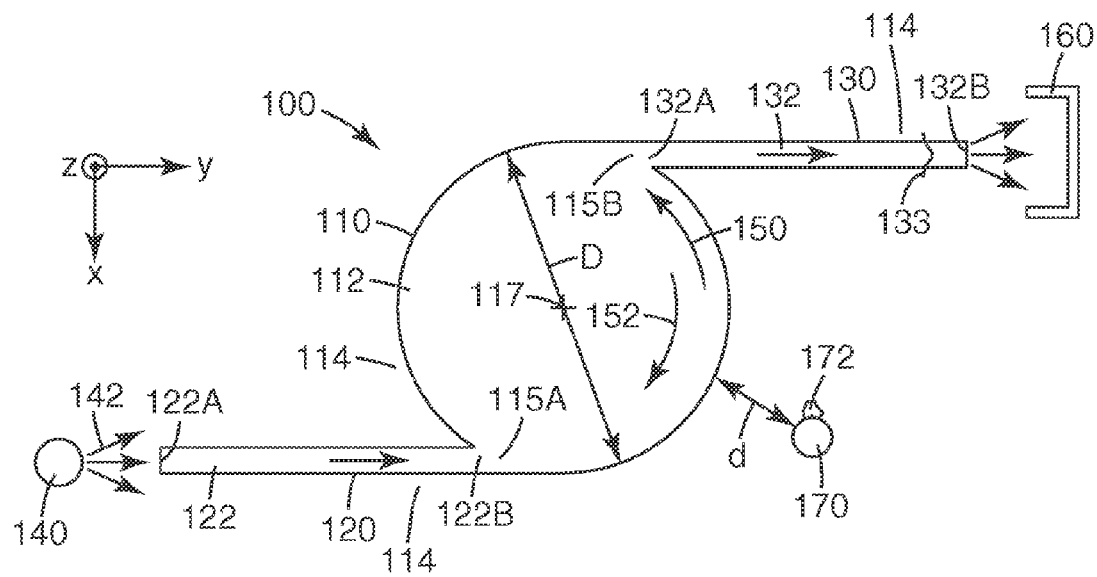
FIGS. 1 and 2 are respective schematic top- and side-views of an optical device.
Figure 2:
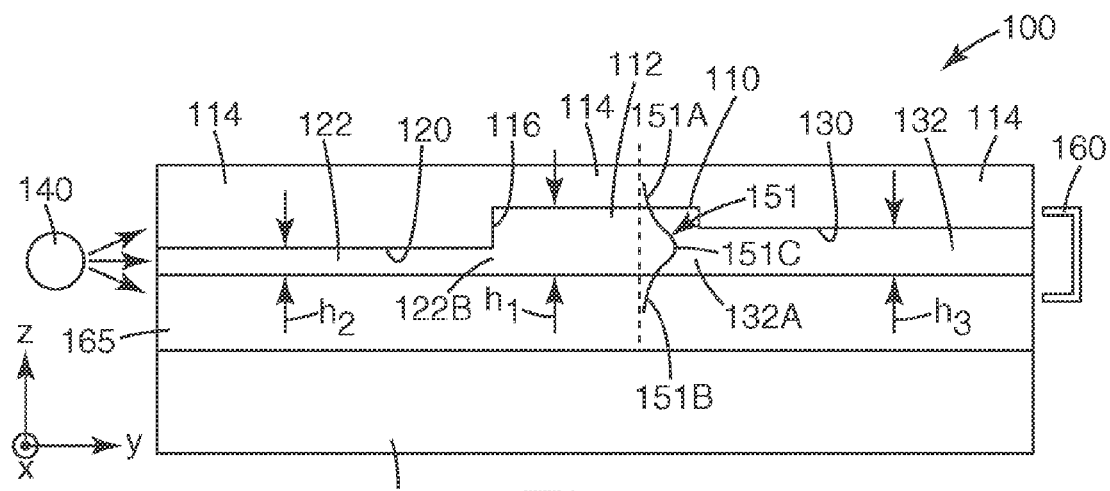

FIGS. 1 and 2 show schematic top- and side-views of an optical device 100, respectively. Optical device 100 includes an optical microresonator 110, a first optical waveguide 120, and a second optical waveguide 130 all disposed on a lower cladding layer 165 disposed on a substrate 161.

In some cases, microresonator 110 is capable of quantizing the allowed optical modes of the microresonator into discrete modes by imposing one or more boundary conditions, such as one or more periodicity conditions. In some cases, microresonator 110 is capable of supporting at least two different guided optical modes such as first guided optical mode 150 and second guided optical mode 152, where guided optical mode 152 is different than guided optical mode 150. In some cases, modes 150 and 152 have the same wavelength.

As used herein, for a given optical configuration such as optical device 100, an optical mode refers to an allowed electromagnetic field in the optical configuration; radiation or radiation mode refers to an optical mode that is unconfined in the optical configuration; a guided mode refers to an optical mode that is confined in the optical configuration in at least one dimension due to the presence of a high refractive index region; and a resonant mode refers to a guided mode that is subject to an additional boundary condition requirement in the optical configuration, where the additional requirement is typically periodic in nature.

Resonant modes are typically discrete guided modes. In some cases, a resonant mode can be capable of coupling to a radiation mode. In some other cases, a resonant mode can have a component that is radiation and is not confined. In general, a guided mode of microresonator 110 can be a resonant or a non-resonant mode. For example, optical modes 150 and 152 can be resonant modes of microresonator 110.

In some cases, first guided optical mode 150 and/or second guided optical mode 152 is capable of propagating within the microresonator while maintaining a same electric field profile. In such cases, the shape or profile of the propagating mode remains substantially the same even if the mode gradually loses energy because of, for example, absorption or radiation losses.

In general, microresonator 110 may be single mode or multimode along a particular direction. For example, microresonator 110 can be single or multimode along the thickness direction (e.g., the z-direction) of the microresonator. In some cases, such as in the case of a sphere- or disc-shaped microresonator, the microresonator can be single or multimode along a radial direction. In some cases, such as in the case of a disk-shaped microresonator, guided optical modes 150 and 152 of microresonator 110 can be azimuthal modes of the microresonator.

Microresonator 110 includes a core or cavity 112 disposed between lower cladding 165 and an upper cladding 114. Core 112 has an average thickness $h_1$. In general, for an electric field associated with a mode of microresonator 110, the evanescent tails of the field are located in the cladding regions of the microresonator and the peak(s) or maxima of the electric field are located in the core region of the microresonator. For example, as schematically shown in FIG. 2, a guided mode 151 of microresonator 110 has an evanescent tail 151A in upper cladding 114, an evanescent tail 151B in lower cladding 165, and a peak 151C in core 112. Guided optical mode 151 can, for example, be mode 150 or 152 of the microresonator.

In the exemplary optical device 100, core 112 is disposed between two cladding layers 114 and 165. In general, microresonator 110 can have one or more upper cladding layers and one or more lower cladding layers. In some cases, lower cladding layer 165 may not be present in optical device 100. In such cases, substrate 161 can be a lower cladding layer for microresonator 110. In some other cases, microresonator 110 does not include upper cladding layer 114. In such cases, an ambient medium, such as ambient air, can form the upper cladding of the microresonator.

Core 112 has an index of refraction $n_m$, cladding 114 has an index of refraction $n_{uc}$, and cladding 165 has an index of refraction $n_{1c}$. In general, $n_m$ is greater than $n_{uc}$ and $n_{1c}$ for at least one wavelength of interest and along at least one direction. In some applications, $n_m$ is greater than $n_{uc}$ and $n_{1c}$ in a wavelength range of interest. For example, $n_m$ can be greater than $n_{uc}$ and $n_{1c}$ for wavelengths in a range from about 400 nm to about 1200 nm. As another example, $n_m$ can be greater than $n_{uc}$ and $n_{1c}$ for wavelengths in a range from about 700 nm to about 1500 nm.

Microresonator core 112 has an input port 115A and an output port 115B, where output port 115B is different than input port 115A. For example, in the exemplary optical device 100, input port 115A and output port 115B are located at different locations around an outer surface 116 of core 112.

Each of the first and second optical waveguides 120 and 130 has a core disposed between multiple claddings. For example, first optical waveguide 120 has a core 122 having a thickness $h_2$ and disposed between upper cladding 114 and lower cladding 165. Similarly, second optical waveguide 130 has a core 132 having a thickness $h_3$ disposed between upper cladding 114 and lower cladding 165.

Core 122 has an index of refraction $n_{w1}$ which is, in general, greater than $n_{uc}$ and $n_{1c}$. Similarly, core 132 has an index of refraction $n_{w2}$ which is, in general, greater than $n_{uc}$ and $n_{1c}$.

In some cases, cores 112, 122, and 132 may be made of different core materials having the same or different indices of refractions. In some other cases, cores 112, 122, and 132 may form a unitary construction, meaning that the cores form a single unit with no physical interfaces between connecting cores. In a unitary construction, the cores may be made of the same core material. A unitary construction can be made using a variety of known methods such as etching, casting, molding, embossing, and extrusion.

Core 122 has an input face 122A and an output face 122B. Input face 122A is in optical communication with a light source 140. Output face 122B physically contacts input port 115A of core 112. In some cases, such as in a unitary construction, output face 122B can be the same as input port 115A. In some cases, there is significant overlap between output face 122B and input port 115A. In some cases, one of output face 122B and input port 115A completely covers the other. For example, in some cases, output face 122B is larger than and completely covers input port 115A of the microresonator.

Core 132 has an input face 132A and an output face 132B. Output face 132B is in optical communication with an optical detector 160. Input face 132A is in physical contact with output port 115B of core 112 of microresonator 110.

Light source 140 is capable of emitting light beam 142, at least a portion of which enters first optical waveguide 120 through input face 122A. In some cases, light entering optical waveguide 120 from light source 140 can propagate along the waveguide as a guided mode of the waveguide. First optical waveguide 120 and input port 115A are so positioned, for example, relative to each other and/or the microresonator, that light traveling in first optical waveguide 120 along the positive y-direction toward input port 115A is capable of coupling primarily to first guided optical mode 150 of the microresonator but not to second guided optical mode 152 of the microresonator. For example, light propagating along optical waveguide 120 and reaching output face 122B is capable of exciting primarily first guided optical mode 150 but not second guided optical mode 152. In some cases, there may be some optical coupling between light propagating in optical waveguide 120 and guided optical mode 152. Such coupling may be by design or due to, for example, optical scattering at input port 115A. As another example, such coupling may be due to optical scattering from manufacturing or fabrication defects. In cases where there is some optical coupling between light propagating in optical waveguide 120 and guided optical mode 152, the propagating light primarily couples to optical mode 150.

Second optical waveguide 130 and output port 115B are so positioned, for example, relative to one another and the microresonator, that light traveling in second optical waveguide 130 along the positive y-direction away from output port 115B is capable of coupling primarily to second guided optical mode 152 of the microresonator but not to first guided optical mode 150 of the microresonator. For example, guided mode 152 at or near output port 115B is capable of exciting a guided mode 133 in the second optical waveguide propagating along the positive y-direction toward output face 132B. In contrast, guided optical mode 150 is not capable of or is weakly capable of exciting guided mode 133. In some cases, there may be some optical coupling between guided optical mode 150 and guided mode 133 due to, for example, optical scattering at output port 115B. But any such coupling is secondary to the optical coupling between guided modes 152 and 133.

In the exemplary optical device 100 of FIGS. 1 and 2, microresonator 110 and optical waveguides 120 and 130 have different thicknesses. In general, thicknesses $h_1$, $h_2$, and $h_3$ may or may not have the same value. In some applications, microresonator 110 and optical waveguides 120 and 130 have the same thickness.

Optical waveguides 120 and 130 can be any type of waveguide capable of supporting an optical mode, such as a guided mode. Optical waveguides 120 and 130 can be one-dimensional waveguides such as planar waveguides, where a one-dimensional waveguide refers to light confinement along one direction. In some applications, optical waveguides 120 and 130 can be two-dimensional waveguides where a two-dimensional waveguide refers to light confinement along two directions. Exemplary optical waveguides include a channel waveguide, a strip loaded waveguide, a rib or ridge waveguide, and an ion-exchanged waveguide.

Figures 3A, 3B:
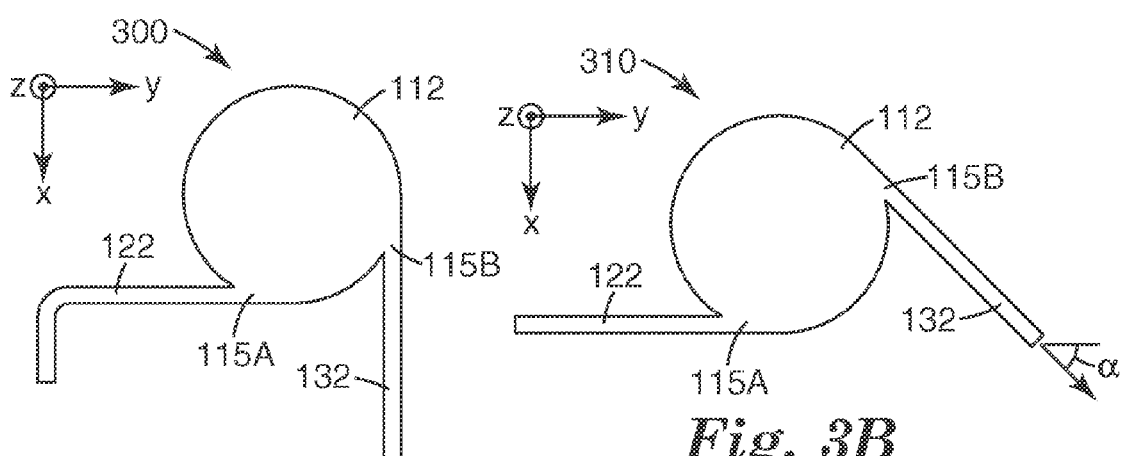
FIGS. 3-5 are schematic top-views of optical devices with different arrangements of optical waveguides.

In the exemplary optical device 100, core 122 of first optical waveguide 120 and core 132 of second optical waveguide 130 are substantially parallel at or near their respective contact points with the microresonator. In particular, both cores 122 and 132 extend along the y-axis at contact points 115A and 115B, respectively. Cores 122 and 132, however, are not collinear. In particular, core 132 is offset relative to core 122 along the x-axis. In general, cores 122 and 132 may or may not be parallel at the input and output ports. Similarly, cores 122 and 132 may or may not be collinear at the input and output ports. For example, in FIG. 3A core 132 is oriented along the x-axis at output port 115B and core 122 extends along the y-axis at input port 115A even though core 122 eventually bends toward the x-axis. As another example, in FIG. 3B core 122 is along the y-axis at input port 115A and core 132 makes an angle α with the y-axis at output port 115B, where the absolute value or magnitude of α can be in a range from about zero degrees to about 180 degrees. In general, α can be positive or negative. Therefore, in general, α can be from about −180 degrees to about 180 degrees. For example, α can be about 45 degrees.

Figure 4:
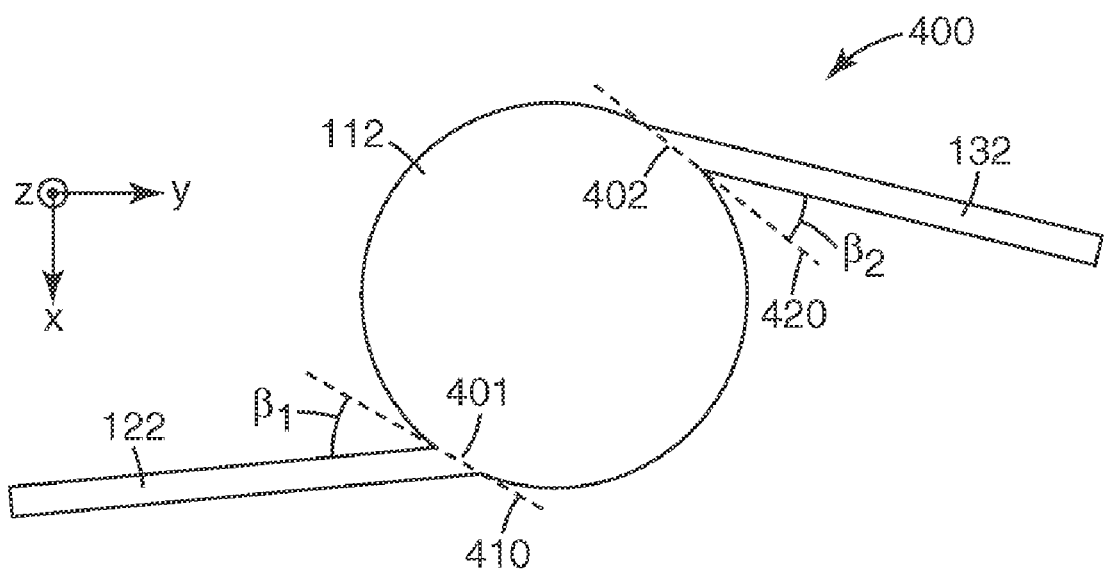

In the exemplary optical devices of FIGS. 1-3, the cores of the two optical waveguides are tangentially connected to the core of the optical microresonator. In general, a core of an optical waveguide may be physically connected to a core of an optical microresonator in any way that may be suitable in an application. For example, FIG. 4 shows an optical device 400 having cores 122 and 132 of optical waveguides 120 and 130 attached to core 112 of microresonator 110 at attachment locations 401 and 402, respectively. Core 122 intersects core 112 at attachment location 401 and makes an angle $\beta_1$ with line 410 tangent to core 112 at location 401. Similarly, core 132 intersects core 112 at attachment location 402 and makes an angle $\beta_2$ with line 420 tangent to core 112 at location 402. Angles $\beta_1$ and $\beta_2$ may or may not be equal. Angles $\beta_1$ and $\beta_2$ may be any angle that may be desirable in an application. In some applications, angles $\beta_1$ and $\beta_2$ are in a range from about zero degrees to about 45 degrees. In some other applications, angles $\beta_1$ and $\beta_2$ are in a range from about zero degrees to about 20 degrees. In some other applications, angles $\beta_1$ and $\beta_2$ are in a range from about zero degrees to about 10 degrees. In still some other applications, angles $\beta_1$ and $\beta_2$ are in a range from about zero degrees to about 5 degrees.

In some cases, at least one of first and second guided optical modes 150 and 152 can be a traveling guided mode of microresonator 110. For example, first and second guided optical modes 150 and 152 may be "whispering gallery modes" (WGMs) of microresonator 110. A WGM is generally a traveling mode confined close to the surface of a microresonator cavity and has relatively low radiation loss. Since the WGMs are confined near the outer surface of the core of a microresonator, they are well-suited to optical coupling with analytes on or near the microresonator surface.

Traveling guided optical modes 150 and 152 can propagate in different, for example opposite, directions. For example, in a disk or sphere microresonator, first guided optical mode 150 can generally travel in a counter clockwise direction and second guided optical mode 152 can generally travel in a clockwise direction. In such a case, first and second guided optical modes 150 and 152 are counter-propagating optical modes.

In some cases, at least one of first and second guided optical modes 150 and 152 can be a standing-wave mode of microresonator 110. A standing-wave mode can be formed by, for example, a superposition of two traveling modes having a proper phase relationship. In some cases, one of the two traveling modes can be a reflection of the other traveling mode.

Light propagating in optical waveguide 120 along the positive y-direction couples primarily to first guided optical mode 150 of microresonator 110. Since core 122 is physically connected to core 112, the optical coupling between first optical waveguide 120 and microresonator 110 is primarily a core coupling and not an evanescent coupling.

An advantage of the present invention is elimination of a coupling gap between at least one optical waveguide and a microresonator. In known microresonators, a gap exists between an optical waveguide and a microresonator. In such cases, the optical coupling between the waveguide and the microresonator is achieved by evanescent coupling. Such a coupling is very sensitive to, among other things, the size of the coupling gap which is typically hard to reproducibly control because of, for example, fabrication errors. Even in fabrication methods where the gap can be controlled with sufficient accuracy, such a control can significantly increase the manufacturing cost. In the present invention, the coupling gap is eliminated by providing direct physical contact between the core of an optical waveguide and the core of an optical microresonator. This can result in reduced manufacturing cost and improved reproducibility.

In some cases, first guided optical mode 150 is launched within microresonator 110 when light from light source 140 enters waveguide 120 through input face 122A and propagates to input port 115A of microresonator 110. When a scattering center 170 is brought sufficiently close to microresonator 110, the scattering center induces an optical scattering between first and second guided optical modes 150 and 152, respectively, resulting in a transfer of energy, or a change in transfer of energy, from guided mode 150 to guided mode 152. If guided mode 152 is already excited in microresonator 110, then the scattering center results in a stronger and more intense guided optical mode 152. If guided mode 152 is not already present in microresonator 110, then the scattering center induces a launching of guided mode 152 by causing optical scattering from first guided mode 150 into second guided mode 152. Guided mode 152 optically couples to optical waveguide 130 at output port 115B resulting in light propagating in waveguide 130 toward output face 132B. Detector 160 detects the transfer of energy between guided modes 150 and 152 and by doing so, is capable of detecting the presence of scattering center 170.

When scattering center 170 is removed from optical proximity to microresonator, the removal induces a change in the optical scattering between first and second guided optical modes 150 and 152, respectively, resulting in a change in transfer of energy from guided mode 152 to guided mode 150. Detector 160 detects the change in transfer of energy from guided mode 152 to guided mode 150 and by doing so, is capable of detecting the removal of scattering center 170.

A change in the strength of optical coupling between scattering center 170 and microresonator 110 can induce a change in the optical scattering between first and second guided optical modes 150 and 152, respectively. The change in the strength of optical coupling can be achieved by various means. For example, a change in the spacing "d" between scattering center 170 and microresonator 110 or core 112 can change the strength of optical coupling between the scattering center and the microresonator. As another example, a change in the index of refraction $n_s$ of the scattering center can change the strength of optical coupling between the scattering center and the microresonator. In general, any mechanism that can cause a change in the strength of optical coupling between scattering center 170 and microresonator 110 can induce a change in the optical scattering between guided modes 150 and 152.

Optical device 100 can be used as a sensor, capable of sensing, for example, an analyte 172. For example, microresonator 110 may be capable of bonding with analyte 172. Such bonding capability may be achieved by, for example, a suitable treatment of the outer surface of microresonator 110. In some cases, analyte 172 is associated with scattering center 170. Such an association can, for example, be achieved by attaching the analyte to the scattering center. The scattering center may be brought in optical proximity to microresonator 110 when analyte 172 bonds with the outer surface of the microresonator. The scattering center induces an optical scattering between first guided optical mode 150 and second guided optical mode 152. The optical scattering results in a change in transfer of energy between the two modes. Optical detector 160 can detect the presence of analyte 172 by detecting the change in transfer of energy between guided modes 150 and 152. Analyte 172 can, for example, include a protein, a virus, or a DNA.

In some cases, analyte 172 can include a first antibody of an antigen that is to be detected. The first antibody can be associated with scattering center 170. A second antibody of the antigen can be associated with microresonator 110. The antigen facilitates a bonding between the first and second antibodies. As a result, the scattering center is brought into optical contact with the microresonator and induces a change in optical scattering within the microresonator. The detector can detect the presence of the scattering center, and therefore, the antigen, by detecting the change in optical scattering. In some cases, the first antibody can be the same as the second antibody. Such an exemplary sensing process can be used in a variety of applications such as in food safety, food processing, medical testing, environmental testing, and industrial hygiene.

In some cases, scattering center 170 can induce a frequency shift in second optical mode 152 where the shift can be detected by detector 160. In some cases, scattering center 170 can induce a frequency shift in first guided optical mode 150. In such cases, detector 160 can be sufficiently sensitive and/or output port 115B can be sufficiently capable of scattering mode 150 into a mode of waveguide 130, so that detector 160 can be capable of detecting the frequency shift in guided mode 150.

Figure 5A:
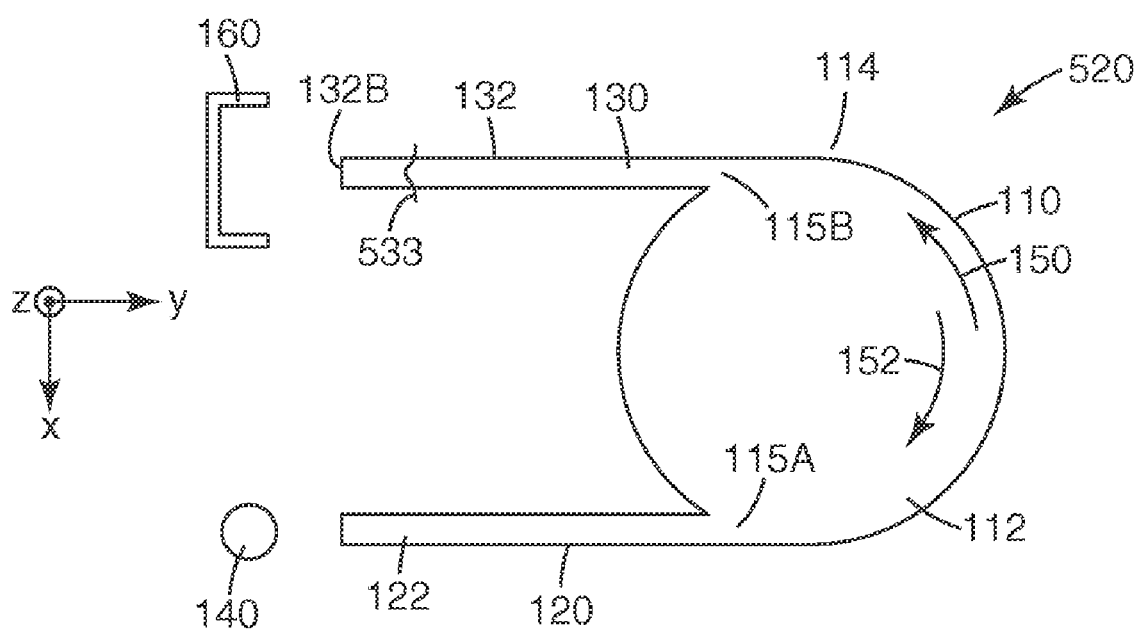

FIG. 5A shows a schematic top-view of an optical device 520. In optical device 520, second optical waveguide 130 and output port 115B are so positioned relative to, for example, one another and/or the microresonator, that light traveling in second optical waveguide 130 along the negative y-direction away from output port 115B is capable of coupling primarily to first guided optical mode 150 of the microresonator but not to second guided optical mode 152 of the microresonator. For example, guided mode 150 at or near output port 115B is capable of exciting a guided mode 533 in the second optical waveguide propagating along the negative y-direction toward output face 132B. In some cases, any optical coupling between guided optical mode 152 and guided mode 533 is substantially weaker than the optical coupling between guide modes 150 and 533. In some cases, the optical coupling between guided optical mode 152 and optical waveguide 130 may be sufficiently strong and/or detector 160 may be sufficiently sensitive so as to permit detection of the optical coupling.

Figure 5B:
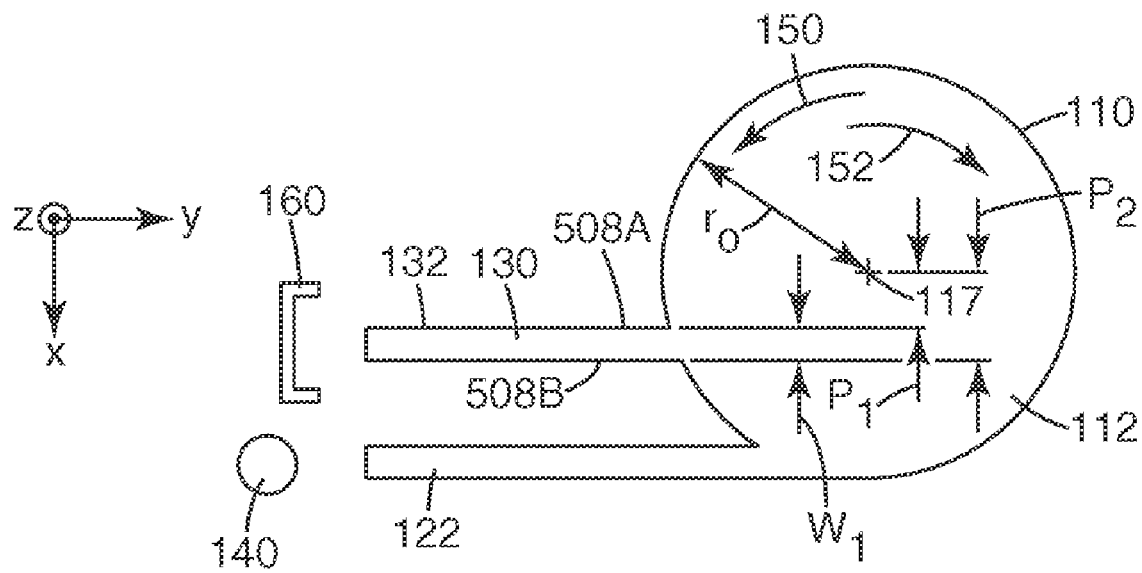

In some cases, the optical coupling between first guided optical mode 150 and optical waveguide 130 may be reduced by reducing the spacing between optical waveguides 120 and 130 by, for example, moving optical waveguide 130 closer to optical waveguide 120 as shown schematically in FIG. 5B. In some cases, core 112 of microresonator 110 has a center 117 and a radius $r_o$. In such cases, center 117 is spaced a distance $P_1$ from a closer edge 508A of core 132 and a distance $P_2$ from a farther edge 508B of core 132. Core 132 of optical waveguide 130 has a width $W_1$ that is equal to $P_2-P_1$. In some cases, $P_2$ is less than or equal to $r_o$. In some cases, the spacing between optical waveguides 120 and 130 is less than $2r_o$.

Figure 5C:
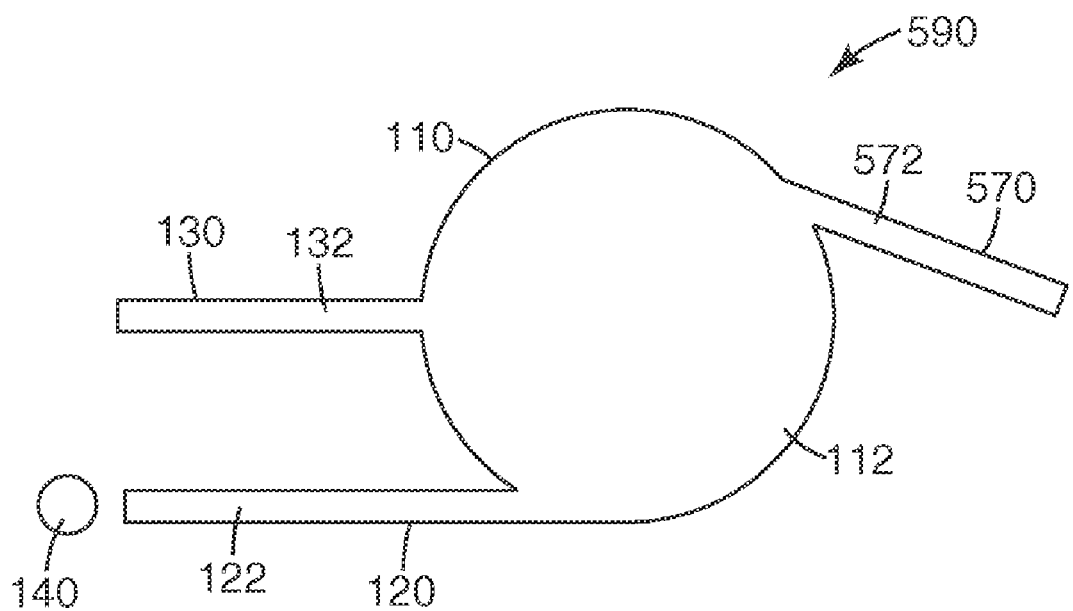

In some cases, optical device 100 may have more than two optical waveguides. For example, FIG. 5C shows a schematic top-view of an optical device 590 having three optical waveguides 120, 130, and 570. In particular, core 122 of first optical waveguide 120, core 132 of second optical waveguide 130, and core 572 of a third optical waveguide 570 each extends from core 112 of microresonator 110.

In some cases, optical device 100 can be capable of detecting a change in the index of refraction of top cladding layer 114. For example, top cladding layer 114 may initially be air resulting in launching of guided mode 150 when light from light source 140 enters first waveguide 120. A change in the index of refraction of top cladding layer 114 can occur when, for example, the air cladding is replaced by or mixed with, for example, a vapor, such as an organic vapor, a gas, a liquid, a biological or chemical material, or any other material that can result in a change in the index of refraction of cladding 114. In some cases, the change in the index of refraction of cladding 114 can induce a frequency shift in guided optical mode 150. The frequency shift may be detected by detector 160.

Microresonator 110 of FIG. 1 is shown to be, for example, a disk microresonator. In general, microresonator 110 can be any type resonator, such as any shape microcavity, capable of supporting at least one guided optical mode and capable of coupling to one or more optical waveguides. In some cases, microresonator 110 has circular symmetry, meaning that the perimeter of a cross-section of core 112 of microresonator 110 can be expressed as a function of distance from a central point only. In some cases, such as in a disk-shaped microresonator, the center point can be the center of the microresonator such as center 117 of microresonator 110. Exemplary microresonator shapes having circular symmetry include a sphere, a disk, and a cylinder.

Figure 6:
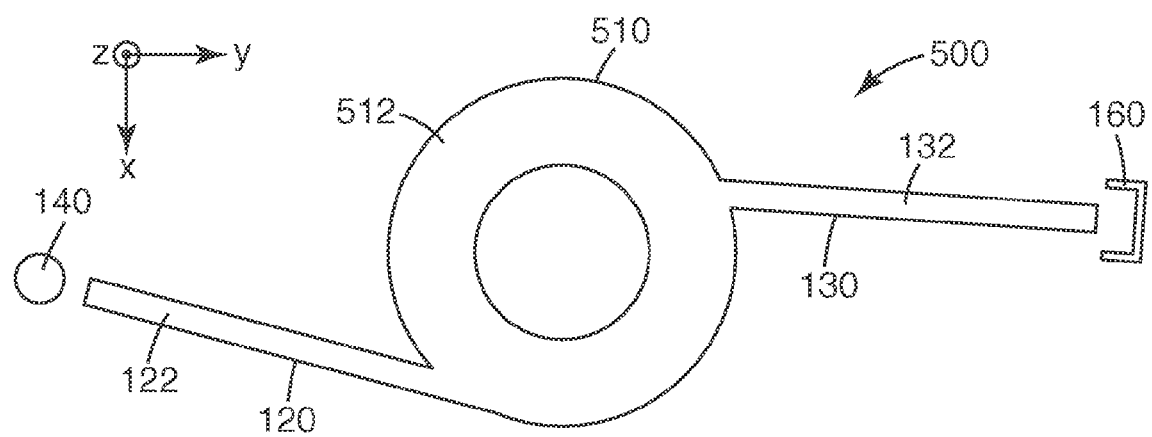
FIGS. 6 and 7 are schematic top-views of optical devices with various closed loop microresonators.

In some cases, microresonator 110 can have spherical symmetry such a sphere-shaped microresonator. In some cases, microresonator 110 can be a closed loop microresonator. For example, FIG. 6 shows a schematic top-view of an optical device 500 that includes a ring microresonator 510 that can, in some cases, be a multimode microresonator. For simplicity and without loss of generality some parts of microresonator 510 are not explicitly shown or identified in FIG. 6. Core 122 of first optical waveguide 120 extends from core 512 of microresonator 510. Similarly, core 132 of second optical waveguide 130 extends from core 512 of microresonator 510. In some cases, microresonator 510 is a multimode microresonator in the radial direction.

Figure 7:
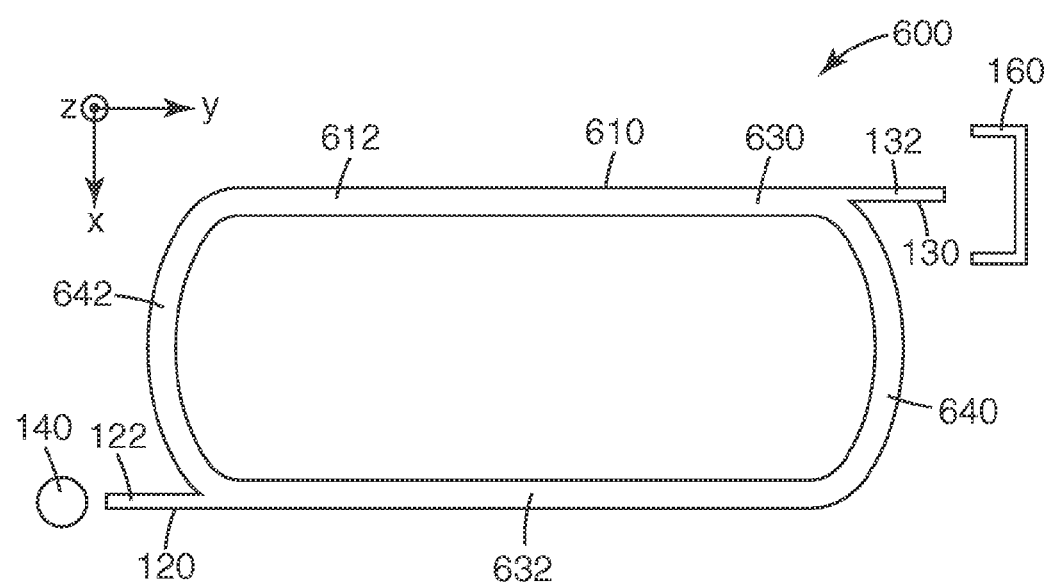

As another example, FIG. 7 shows a schematic top-view of an optical device 600 that includes a racetrack microresonator 610 that can, in some cases, be a multimode microresonator. For simplicity and without loss of generality some parts of microresonator 610 are not explicitly shown or identified in FIG. 7. Core 612 of microresonator 610 has linear portions 630 and 632 and curved portions 640 and 642. Core 122 of first optical waveguide 120 extends from core 612 of microresonator 610. Similarly, core 132 of second optical waveguide 130 extends from core 612 of microresonator 610.

Figure 8:
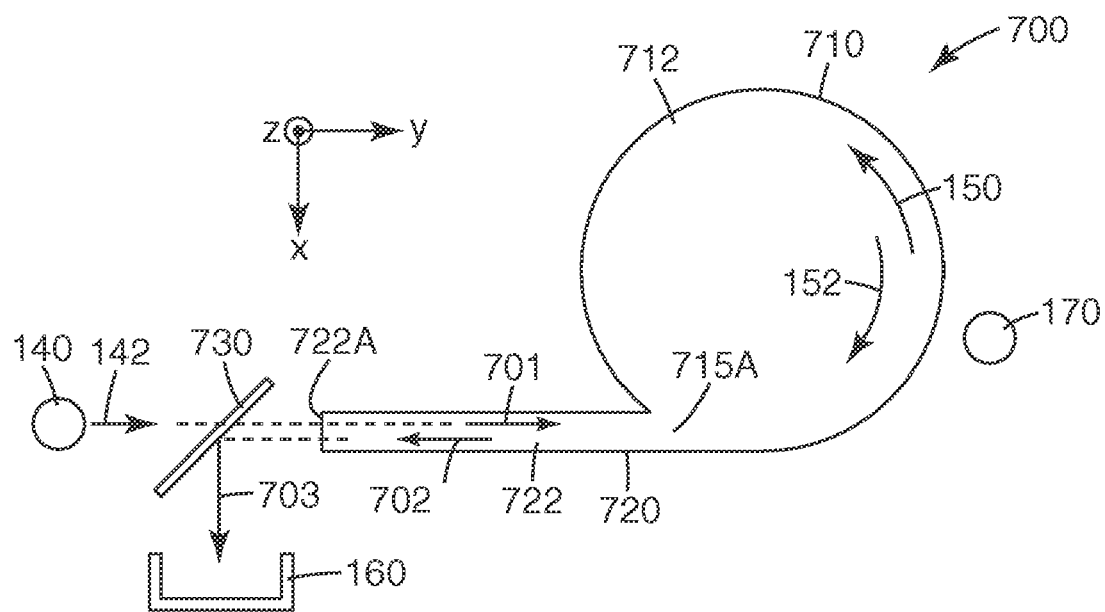
FIG. 8 is a schematic top-view of an optical device.

FIG. 8 shows a schematic top-view of an optical device 700 that includes a microresonator 710 capable of supporting at least first and second guided optical modes 150 and 152, respectively, where second guided optical mode 152 is different than first guided optical mode 150. Optical device 700 further includes an optical waveguide 720. Microresonator 710 has a core 712 and optical waveguide 720 has a core 722. For simplicity and without loss of generality some parts of the microresonator and the optical waveguide, such as the cladding(s), are not explicitly shown or identified in FIG. 8.

Waveguide core 722 has an input face 722A that is in optical communication with light source 140. The other end of core 722 terminates at port 715A of core 712. Optical waveguide 720 and port 715A are so arranged relative to each other and core 712 that light propagating along the positive y-direction in optical waveguide 720, such as light 701, is capable of coupling primarily to first guided optical mode 150 but not second guided optical mode 152 of microresonator 710. Optical waveguide 720 and port 715A are furthermore so arranged that light propagating along the negative y-direction in optical waveguide 720, such as light 702, is capable of coupling primarily to second guided mode 152 but not first guided optical mode 150 of microresonator 710.

In some cases, microresonator 710 has circular symmetry. In some cases, a guided mode of microresonator 710, such as guided optical mode 150, is capable of propagating within microresonator 710 while maintaining a same electric field profile.

Light source 140 is capable of emitting light 142. At least a portion of light 142 enters optical waveguide 720 through input face 722A of the waveguide and propagates along the positive y-axis as light 701. In some cases, light 701 can be a guided mode of optical waveguide 720. At port 715A, light 701 optically couples primarily to and launches first guided optical mode 150 of the microresonator. In some cases, light 701 may weakly couple to and launch second guided optical mode 152, but any such coupling will be weak and secondary to the optical coupling between light 701 and first guided optical mode 150. For example, if light 701 launches both guided modes 150 and 152, guided mode 150 will be substantially more intense than guided mode 152.

When scattering center 170 is brought into optical proximity with microresonator 710, the scattering center induces an optical scattering between first guided optical mode 150 and second guided optical modes 152, resulting in a transfer of energy from guided mode 150 to guided mode 152. If guided mode 152 is currently excited in microresonator 710, then the scattering center results in a stronger and more intense guided optical mode 152. If guided mode 152 is not already present in microresonator 710, then scattering center 170 induces a launching of guided mode 152 by causing optical scattering from first guided mode 150 into second guided mode 152.

Guided optical mode 152 optically couples to optical waveguide 720 by core coupling and propagates inside the waveguide as light 702 toward input face 722A. Optical element 730 redirects at least a portion of light 702 as light 703 towards detector 160. Detector 160 detects the transfer of energy between guided modes 150 and 152 and by doing so, is capable of detecting the presence of scattering center 170.

Optical element 730 redirects by, for example, reflection at least a portion of light 702 along the x-axis while transmitting at least a portion of input light 142. Optical element 730 can be a beam splitter. As another example, optical element 730 can be an optical circulator.

Figure 9:
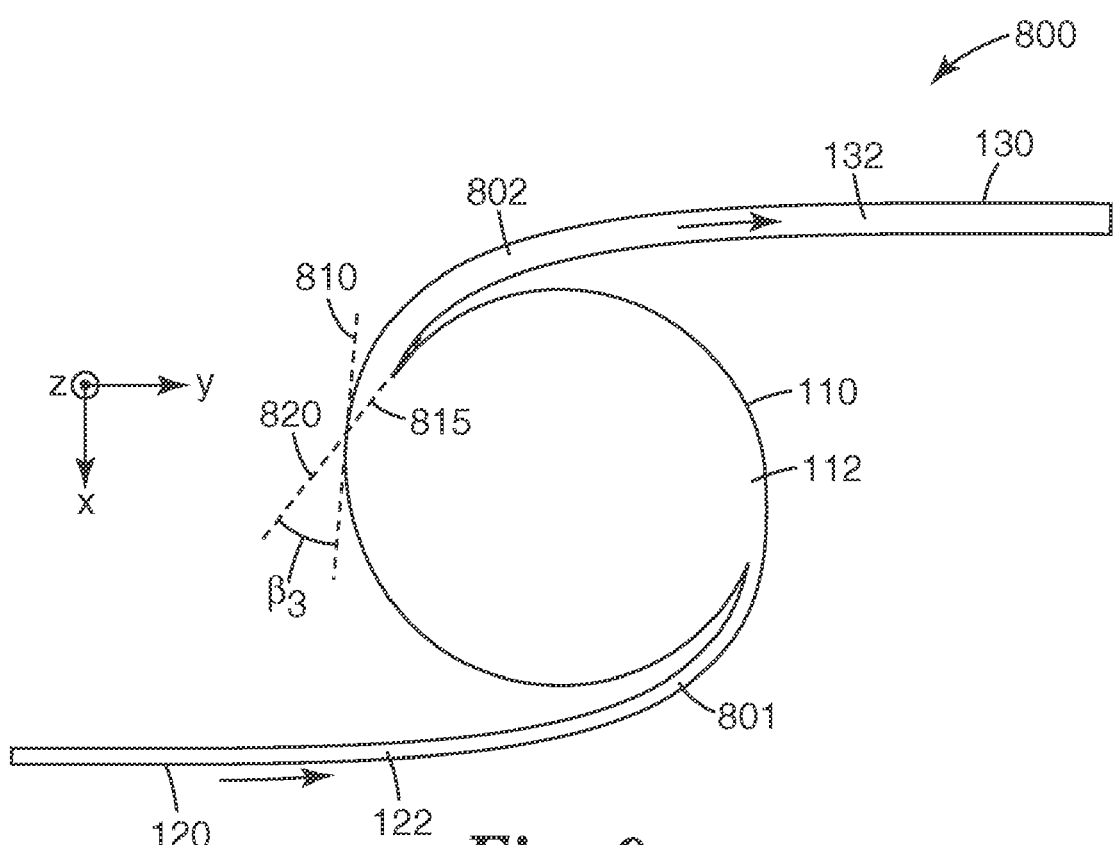
FIG. 9 is a schematic top-view of an optical device with a single optical waveguide.

In the exemplary optical devices shown in FIGS. 1-8, the optical waveguides extend linearly. In general, an optical waveguide coupled to a microresonator can have any shape that may be desirable in an application. For example, in optical device 800 shown schematically in FIG. 9, optical waveguides 120 and 130 have curved portions, such as curved portions 801 and 802. Core 132 of waveguide 130 intersects core 112 of microresonator 110 at an attachment location 815. The angle between cores 132 and 112 is $\beta_3$ defined as the angle between line 810 tangent to core 132 at location 815 and line 820 tangent to core 112 at the same location.

In some cases, the curvature of a curved portion of a waveguide is sufficiently small that the curvature results in no or little radiation loss. In some cases, an optical waveguide coupled to a microresonator can be a nonlinear waveguide, a piecewise linear waveguide, or a waveguide that has linear and nonlinear portions.

In the exemplary embodiment shown in FIGS. 1-2, cores 122, 112, and 132 are substantially in the same plane. In such a case, the core coupling between an optical waveguide and a microresonator can be considered to be a lateral core coupling. For example, optical waveguide 120 laterally core couples to microresonator 110 in core coupling region 122B.

Similarly, optical waveguide 130 laterally core couples to microresonator 110 in core coupling region 132A.

Figure 12A:
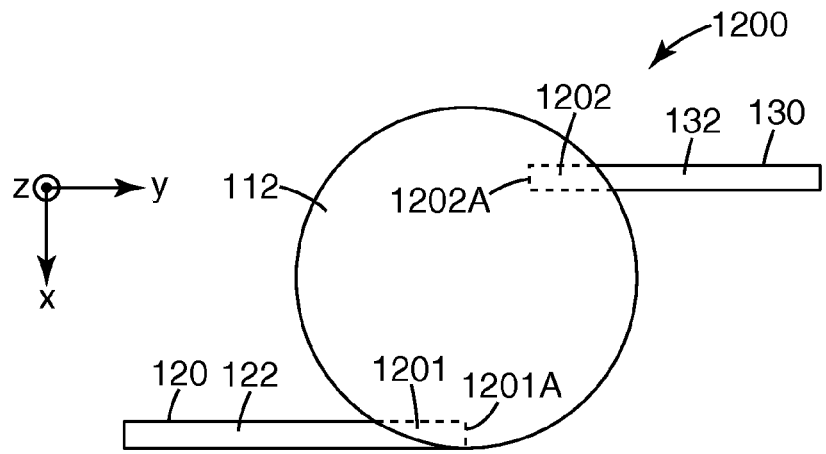
FIGS. 12A and 12B are respective schematic top- and side-views of an optical device with vertical core coupling.
Figure 12B:
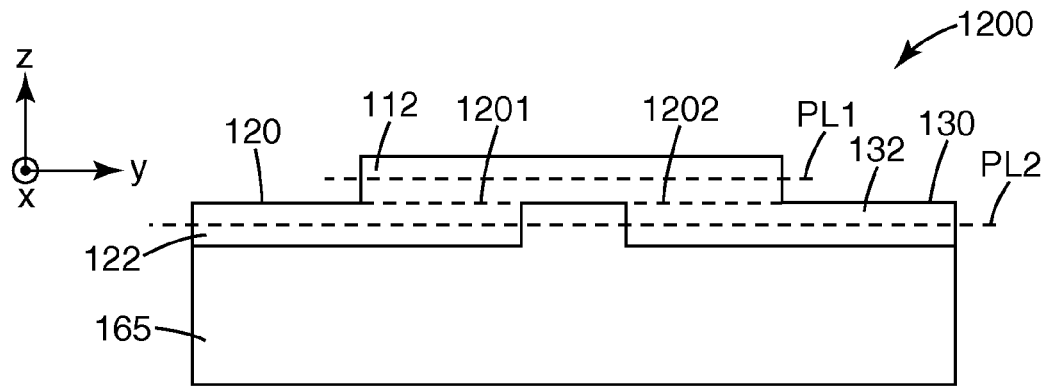

In some cases, a microresonator core and an optical waveguide core may be in substantially different planes. In such cases, the core coupling between the optical waveguide and the microresonator may be considered to be a vertical core coupling. For example, FIGS. 12A and 12B are respective schematic top- and side-views of an optical device 1200 in which microresonator core 112 is positioned in a plane PL1 and optical waveguide cores 122 and 132 are positioned in a plane PL2 different than plane PL1. Optical waveguide 120 vertically core couples to microresonator 110 in a core coupling region 1201, where region 1201 is the region of overlap between cores 112 and 122. Similarly, optical waveguide 130 vertically core couples to microresonator 110 in a core coupling region 1202, where region 1202 is the region of overlap between cores 112 and 132.

In some applications, microresonator 110 and optical waveguides 120 and 130 in optical device 1200 can form a unitary construction and can be fabricated using known fabrication methods such as a molding process.

Figure 12C:
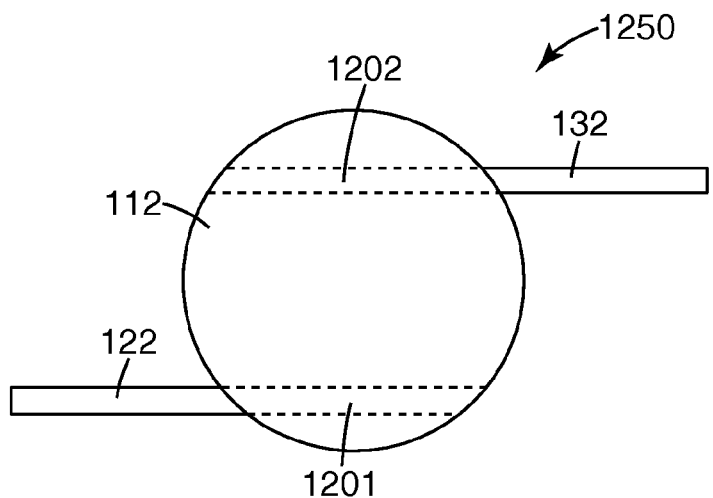
FIG. 12C is a schematic top-view of an optical device with vertical core coupling.

In the exemplary embodiment shown in FIGS. 12A and 12B, optical waveguides 120 and 130 end at termination points 1201A and 1202A, respectively. In general, an optical waveguide may terminate at any location as long as there is an area of overlap between the microresonator core and the optical waveguide core to allow for vertical core coupling. For example, FIG. 12C shows a schematic top-view of an optical device 1250 in which optical waveguide cores 122 and 132 extend across microresonator core 112.

Figure 13A:
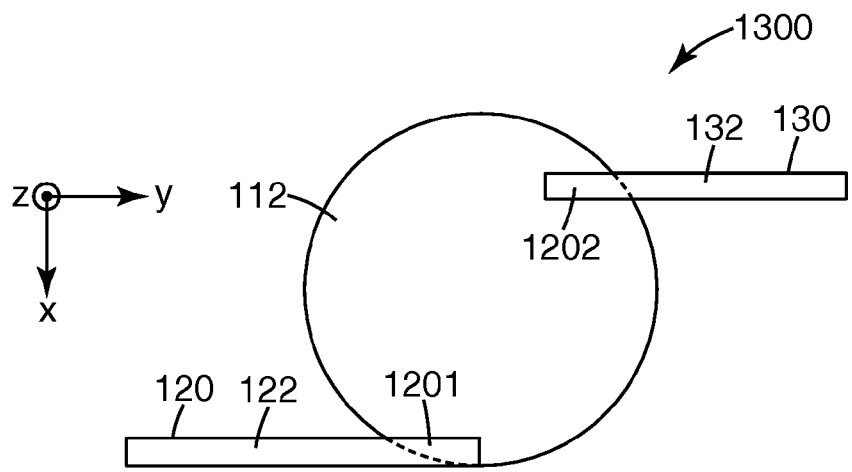
FIGS. 13A and 13B are respective schematic top- and side-views of an optical device with vertical core coupling.
Figure 13B:
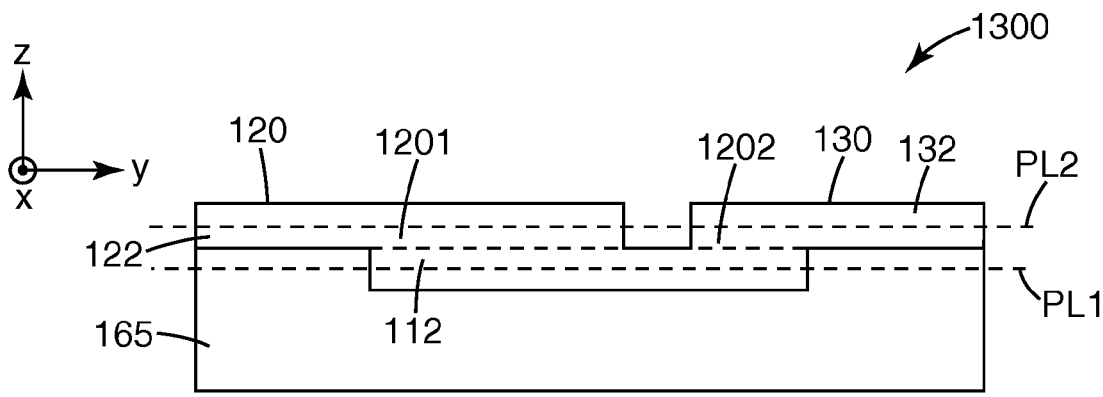

In the exemplary embodiment shown in FIGS. 12A and 12B, optical waveguide cores 122 and 132 are located below microresonator core 112. In general, an optical waveguide that vertically core couples to a microresonator may be positioned above or below the microresonator. For example, FIGS. 13A and 13B show respective schematic top- and side-views of an optical device 1300 in which microresonator core 112 is positioned in a plane PL1 and optical waveguide cores 122 and 132 are positioned in a plane PL2 positioned above plane PL1. Optical waveguides 120 and 130 vertically core couple to microresonator 110 in core coupling regions 1201 and 1202, respectively.

Figure 14:
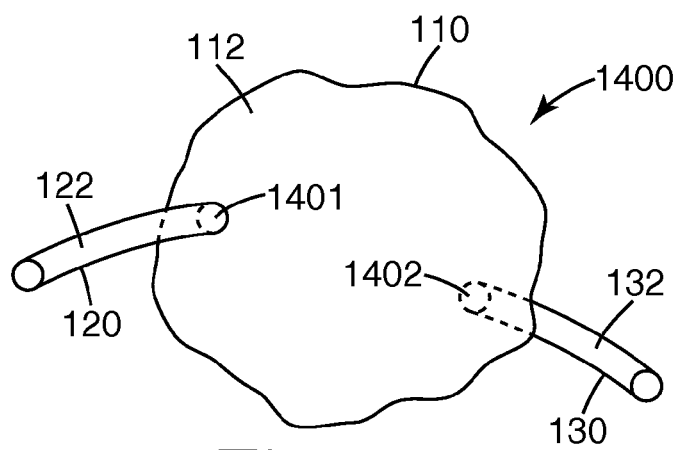
FIG. 14 is a schematic three-dimensional view of an optical device.

In general, an optical waveguide core is so oriented relative to a microresonator core to allow coupling of light between the optical waveguide and the microresonator by a core coupling. For example, FIG. 14 shows a schematic three-dimensional view of an optical device 1400 in which optical waveguide 120 core couples to microresonator 110 in core coupling region 1401 and optical waveguide 130 core couples to microresonator 110 in core coupling region 1402.

Some of the advantages of the disclosed embodiments are further illustrated by the following example. The particular materials, amounts and dimensions recited in this example, as well as other conditions and details, should not be construed to unduly limit the present invention. An optical device similar to optical device 100 of FIGS. 1 and 2 was numerically analyzed using an effective two dimensional Finite Difference Time Domain (FDTD) approach. For the simulation, microresonator core 112 was silicon in the shape of a disk having a core diameter D equal to 3.6 microns, a core thickness $h_1$ of 0.2 microns, and a core index of refraction of 3.5. Cores 122 and 132 were each silicon with a thickness of 0.2 microns and an index of refraction of 3.5. Upper cladding 114 was water with an index of refraction equal to 1.33. Lower cladding 165 was silicon dioxide with a thickness of 3 microns and an index of refraction of 1.46. Substrate 161 was dilicon with an index of refraction equal to 3.5.

Light source 140 was a pulsed light source emitting light 142 in the form of discrete 1 femtosecond long Gaussian pulses centered at wavelength 2 microns with a full width at half maximum (FWHM) of 1.5 microns. The broadband input pulses resulted in a wide spectrum response in the range from about 1 micron to about 3 microns detected by detector 160.

Figure 10A:
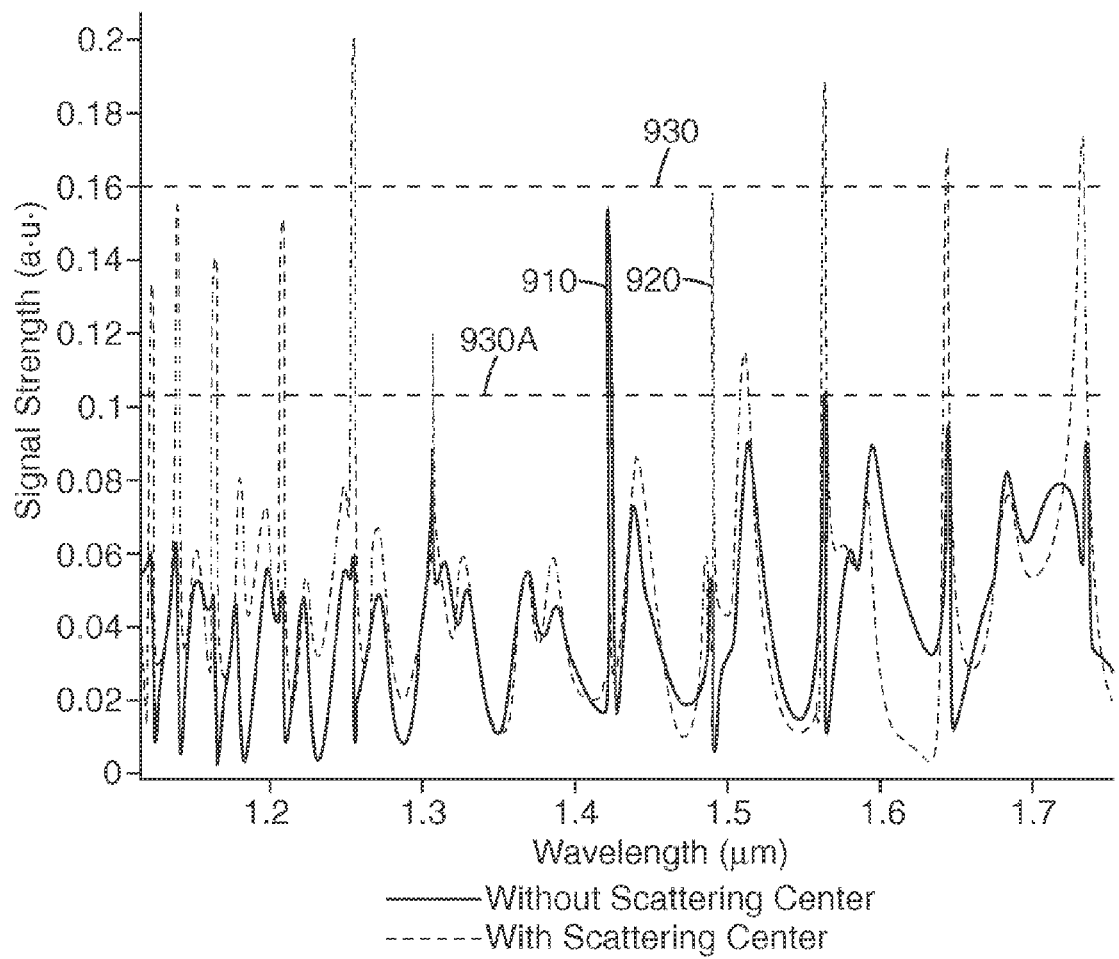
FIG. 10A is a plot of a calculated output signal strength as a function of wavelength.

FIG. 10A shows the calculated signal strength (in arbitrary units relative to the intensity of input light) at detector 160 as a function of wavelength (in microns). Curve 910 shows the signal strength in the absence of scattering center 170. Curve 920 shows the signal strength in the presence of scattering center 170. In generating curve 920, the scattering center was a solid spherical gold nanoparticle in physical contact with microresonator 110. Scattering center 170 had real and imaginary indices of refraction of 0.54 and 9.58, respectively. The diameter of the scattering center was 80 nanometers. Curves 910 and 920 show that the output spectrum at detector 160 changes substantially when scattering center 170 is brought into contact with the microresonator.

FIG. 10A shows that the microresonator has high Q-factors at several wavelengths. For example, the numerical analysis showed that the Q-factor of the microresonator was 1424 at 1.43 microns, 1240 at 1.49 microns, and 781 at 1.56 microns. Q-factor can be defined as $\lambda_o/\Delta\lambda_o$ where $\lambda_o$ is the center (resonant) wavelength and $\Delta\lambda_o$ is the full width at half maximum (FWHM).

Figure 10B:
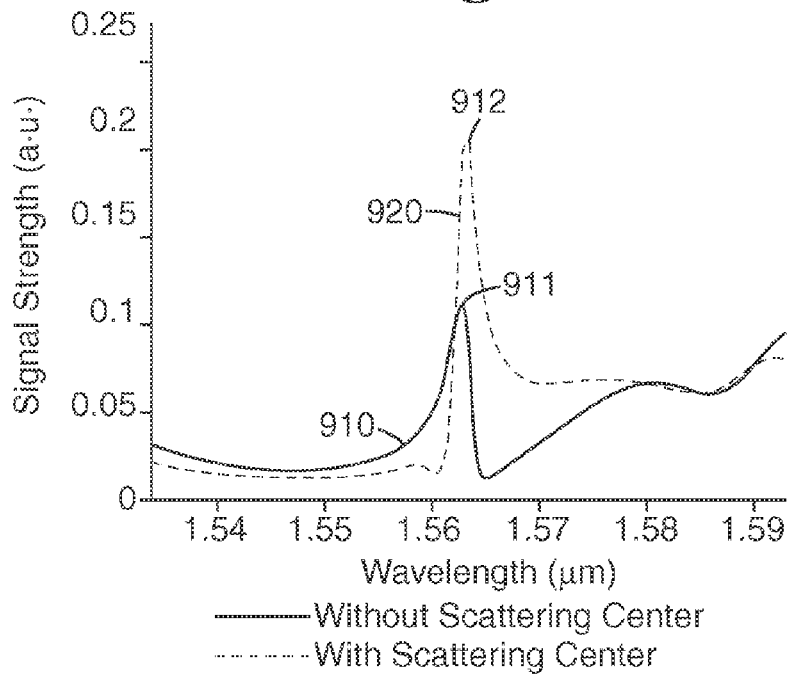
FIG. 10B is a magnified view of a portion of the plot in FIG. 10A.

FIG. 10B is an expanded view of curves 910 and 920 near 1.56 microns showing that scattering center 170 resulted in a relatively large shift of about 0.7 nanometers from peak 911 to peak 912. An advantage of the disclosed embodiments is that the presence of a scattering center in optical proximity to a microresonator can result in a relatively large shift in a peak of the output spectrum at detector 160. In some cases, the shift can be greater than 0.1 nanometers, or greater than one nanometer, or greater than 2 nanometers, or greater than 5 nanometers.

In some applications, light source 140 can be a broadband light source emitting, for example, white light. Similarly, detector 160 can be a broadband detector. In such cases, detector 160 can signal the presence of a scattering center if the overall detected light intensity is above a pre-determined intensity threshold. For example, referring to FIG. 10A, a detected intensity level larger than an intensity threshold level 930 set at about 0.16 can indicate the presence of scattering center 170. In some cases, the threshold level can be set a lower level, such as at a threshold level 930A, to include a small fraction of signal strength 910 while rejecting a substantial portion of signal strength 910 as background noise. An advantage of broadband light sources and detectors is reduced overall device cost.

Figure 11:
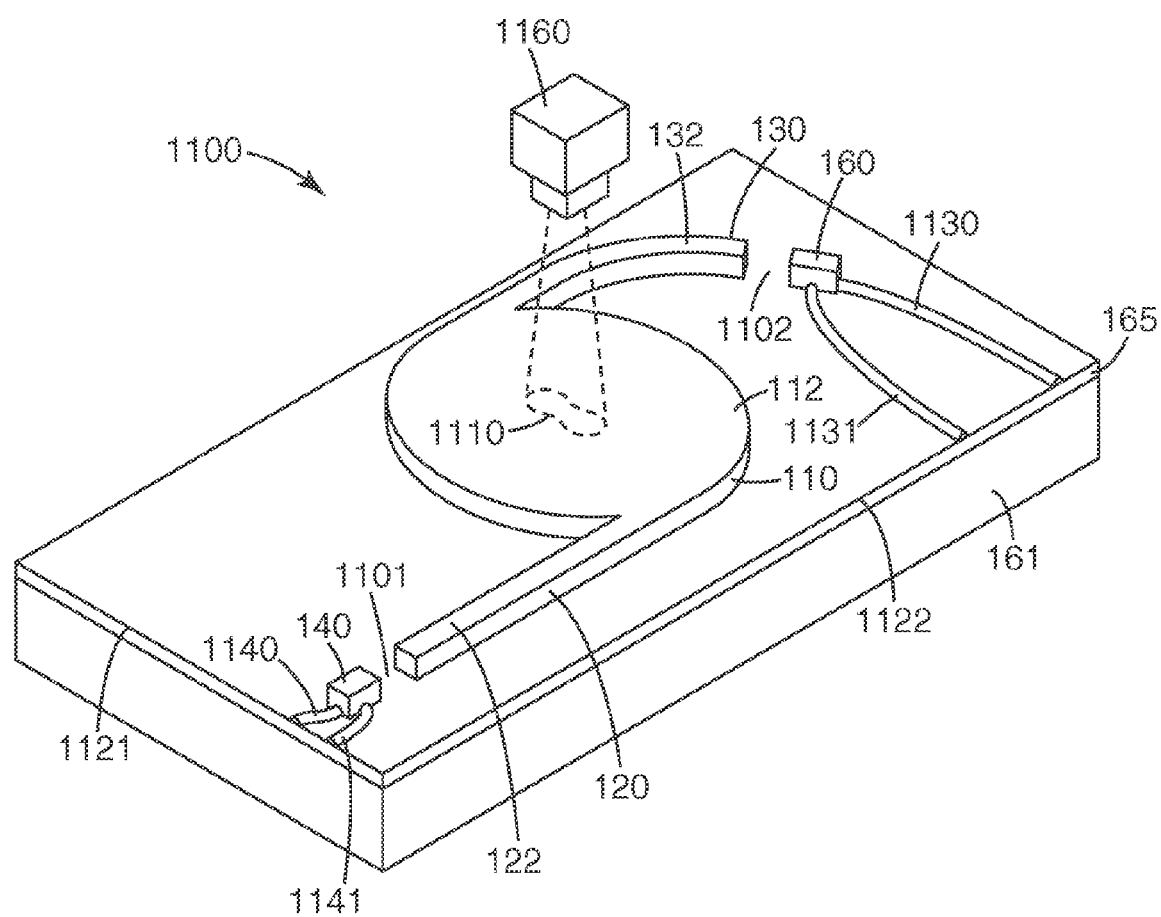
FIG. 11 is a schematic three-dimensional view of an integrated optical device.

FIG. 11 shows a schematic three-dimensional view of an integrated optical device 1100. Light source 140 and detector 160 are integrated onto substrate 161 of optical device 1100. Light source 140 is separated from waveguide 120 by a gap 1101 and includes electric leads 1140 and 1141 integrated onto substrate 161. Electric leads 1140 and 1141 extend to an edge 1121 of optical device 1100 for connection to, for example, an external power source and/or a controller not shown in FIG. 11. Detector 160 is separated from waveguide 130 by a gap 1102 and includes electric leads 1130 and 1131 integrated onto substrate 161. Electric leads 1130 and 1131 extend to an edge 1122 of optical device 1100 for connection to, for example, an external power source and/or other electronics not shown in FIG. 11.

In some applications, a light detector, such as a camera 1160, may be employed to monitor the optical intensity level in a particular area of microresonator 110. For example, camera 1160 can image and monitor the light intensity magnitude and/or profile in an area 1110 near, for example, the center of microresonator 110. In some cases, area 1110 can be capable of extracting light from the microresonator. For example, area 1110 can be roughened or structured to scatter light. As another example, area 1110 can be coated with a high index material to allow light extraction in that area. In such a case, camera 1160 may be placed in direct contact with the high index material.

In the absence of a light scattering center, the light intensity level in area 1110 can be quite low. For example, the guided modes propagating within the microresonator can be WGMs substantially confined to the sides of core 112 of microresonator 110. When a 30 scattering center is brought into optical contact with a side of the microresonator, the scattering center can scatter light that is propagating within the microresonator in different directions including towards area 1110. Area 1110 can receive and out couple the scattered light towards camera 1160. Camera 1160 can detect the presence of the scattering center by detecting the out coupled light.

Microresonator 110 and optical waveguides 120 and 130 can be made using known fabrication techniques. Exemplary fabrication techniques include photolithography, printing, casting, extrusion, and embossing. Different layers in optical device 100 can be formed using known methods such as sputtering, vapor deposition, flame hydrolysis, casting, or any other deposition method that may be suitable in an application.

Substrate 161 can be rigid or flexible. Substrate 161 may be optically opaque or transmissive. The substrate may be polymeric, a metal, a semiconductor, or any type of glass. For example, substrate 161 can be silicon. As another example, substrate 161 may be float glass or it may be made of organic materials such as polycarbonate, acrylic, polyethylene terephthalate (PET), polyvinyl chloride (PVC), polysulfone, and the like.

Examples of scattering centers that can be appropriate for use with the disclosed embodiments include silicon nanoparticles and metal nanoparticles, including gold and aluminum nanoparticles. In some cases, a scattering center may be a semiconductor such as Si, GaAs, InP, CdSe, or CdS. For example, a scattering center can be a silicon particle having a diameter of 80 nanometers and an index of refraction (the real part) of 3.5 for a wavelength of interest. Another example of a scattering center is a gold particle having a diameter of 80 nanometers and an index of refraction of 0.54+9.58i for wavelengths near 1550 nm. Another example of a scattering center is an aluminum particle having a diameter of 80 nanometers and an index of refraction of 1.44+16.0i for wavelengths near 1550 nm.

In some cases, the scattering center can be a dielectric particle. In some cases, the scattering center can be a fluorescent particle. In some other cases, the scattering center can be a non-fluorescent particle.

In some cases, the size of scattering center 170 is no greater than 1000 nanometers, or no greater than 500 nanometers, or no greater than 100 nanometers.

As used herein, terms such as "vertical", "horizontal", "above", "below", "left", "right", "upper" and "lower", and other similar terms, refer to relative positions as shown in the figures. In general, a physical embodiment can have a different orientation, and in that case, the terms are intended to refer to relative positions modified by the actual orientation of the device. For example, even if the construction in FIG. 2 is inverted as compared to the orientation in the figure, lower cladding 165 is still considered to be "below" upper cladding 114.

While specific examples of the invention are described in detail above to facilitate explanation of various aspects of the invention, it should be understood that the intention is not to limit the invention to the specifics of the examples. Rather, the intention is to cover all modifications, embodiments, and alternatives falling within the spirit and scope of the invention as defined by the appended claims.

What is claimed is:

1. An optical device comprising:
   a microresonator having a circular symmetry, the microresonator having a core having input and output ports, the output port being different than the input port; and
   first and second optical waveguides, each optical waveguide having a core, the core of the first optical waveguide terminating at the input port of the core of the microresonator, the core of the second optical waveguide terminating at the output port of the core of the microresonator, the microresonator and the first and second optical waveguides forming a unitary construction, the first and second optical waveguides not being collinear at their termination points at the microresonator.

2. The optical device of claim 1, wherein at least one of the first and second optical waveguides is capable of optically coupling to the microresonator by a core coupling.

3. The optical device of claim 1, wherein the microresonator is a sphere.

4. The optical device of claim 1, wherein the microresonator is a cylinder.

5. The optical device of claim 1, wherein the microresonator is a disc.

6. The optical device of claim 1, wherein the microresonator is a ring.

7. The optical device of claim 1, wherein at least one of the first and second optical waveguides is a planar waveguide.

8. The optical device of claim 1, wherein at least one of the first and second optical waveguides is a two-dimensional waveguide.

9. The optical device of claim 1, wherein
   the microresonator is capable of supporting first and second guided optical modes, the second guided optical anode being different than the first guided optical mode; herein
   the first optical waveguide and the input port of the core of the microresonator are arranged so that light traveling in the first optical waveguide toward the input port is capable of coupling primarily to the first but not the second guided optical mode of the microresonator; and wherein
   the second optical waveguide and the output port of the core of the microresonator are arranged so that light traveling in the second optical waveguide away from the output port is capable of coupling primarily to the second but not the first guided optical mode of the microresonator.

10. The optical device of claim 9, wherein at least one of the first and second guided optical modes of the microresonator is a traveling mode.

11. The optical device of claim 9, wherein each of the first and second guided optical modes of the microresonator is a traveling mode.

12. The optical device of claim 11, wherein the first and second guided optical modes of the microresonator travel in generally opposite directions.

13. The optical device of claim 9, wherein at least one of the first and second guided optical modes is capable of propagating within the microresonator while maintaining a safe, electric field profile.

14. The optical device of claim 9, wherein light traveling in the first optical waveguide toward the input port couples to the first guided optical mode by a core coupling.

15. The optical device of claim 9, wherein light traveling in the second optical waveguide away from the output pod couples to the second guided optical mode by a core coupling.

16. The optical device of claim 9, wherein at least one of the first and second guided optical modes of the microresonator is a resonant mode of the microresonator.

17. The optical device of claim 9, such that when a scattering center is brought into optical proximity with the microresonator, the optical proximity induces an optical scattering between the first and second guided optical modes.

18. The optical device of claim 9 further comprising a scattering center optically coupled to the microresonator.

19. The optical device of claim 18, wherein a change in a strength of optical coupling between the scattering center and the microresonator induces a change in an optical scattering between the first and second guided optical modes.

20. The optical device of claim 19, wherein a change in a spacing between the scattering center and the microresonator changes the strength of optical coupling between the scattering center and the microresonator.

21. The optical device of claim 19, wherein a change in an index of refraction of the scattering center changes the strength of optical coupling between the scattering center and the microresonator.

22. The optical device of claim 17, wherein the scattering center comprises a nanoparticle.

23. The optical device of claim 22, wherein a size of the nanoparticle is less than about 500 nanometers.

24. The optical device of claim 22, wherein size of the nanoparticle is less than about 300 nanometers.

25. The optical device of claim 22, wherein the nanoparticle comprises a metal.

26. The optical device of claim 25, wherein the metal comprises gold.

27. A sensor comprising:
the optical device of claim 1;
a light source capable of emitting light, the first optical waveguide receiving the light through the an input face at the first optical waveguide; and
a detector capable of detecting light that exits the second optical waveguide through an output face of the second optical waveguide.

28. An optical device comprising:
a light source;
an optical detector;
a microresonator having a circular symmetry and being capable of supporting first and second guided counter traveling optical modes, the second guided optical mode being different than the first guided optical mode, the microresonator having a core, the core having input and output ports, the output port being different than the input port, the microresonator being capable of bonding with an analyte associated with a scattering center;
a first untied waveguide having a core, optical having an in optical communication with the light source and terminating at the input port of the core of the microresonator; and
a second optical waveguide having a core, having terminating at the output port of the core of the microresonator and in optical communication with the optical detector, the microresonator and the first and second optical waveguides forming a unitary construction;
such that when the associated analyte bonds with the microresonator, the scattering center is capable of inducing an optical scattering between the fiat and second guided optical anodes, the optical scattering resulting in a transfer of energy from the first guided mode to the second guided mode, the optical detector detecting the transfer of energy.

29. The optical device of claim 28, wherein the analyte comprises an antibody.

30. An optical device comprising:
a microresonator capable of supporting at least two resonant optical modes, at least one of the two resonant modes being capable of propagating within the microresonator while maintaining a same electric field profile; and
first end second optical waveguides terminating at the microresonator and capable of coupling to the microresonator by a core coupling, the microresonator and the first and second optical waveguides forming a unitary construction, the first and second optical waveguides not being collinear at their termination points at the microresonator.

31. The optical device of claim 30, wherein the microresonator is a racetrack.

32. The optical device of claim 30, wherein the microresonator is a disk.

33. An optical device comprising:
a microresonator having a core;
a first optical waveguide having a core terminating at a first location on the core of the microresonator; and
a second optical waveguide having a core terminating at a second location on the core of the microresonator, the second location being different from the first location, the microresonator end the first and second optical waveguides forming a unitary construction, the first and second optical waveguides not being collinear at their termination points at the microresonator.

34. The optical device of claim 33, wherein the first location and the first optical waveguide are arranged so that light traveling in the first optical waveguide toward the first location is capable of coupling primarily to a first but not a second guided optical mode of the microresonator, and wherein the second location and the second optical waveguide are arranged so that light traveling in the second optical waveguide away from the second location is capable of coupling primarily to the second but not the first guided optical mode of the microresonator.

35. The optical device of claim 33, wherein the microresonator is capable of supporting at least first and second guided optical modes, the second guided optical mode being different than the first guided optical mode, at least one of the at least first and second guided optical modes being capable of propagating within the microresonator while maintaining a same electric field profile.

36. The optical device of claim 33, wherein the microresonator has a circular symmetry.

37. The optical device of claim 33, wherein the microresonator core has a center and a radius, a spacing between the center and an outer edge of the core of at least one of the first and second optical waveguides being less than the radius.

* * * * *

UNITED STATES PATENT AND TRADEMARK OFFICE
CERTIFICATE OF CORRECTION

| | | |
|---|---|---|
| PATENT NO. | : 7,702,202 B2 | |
| APPLICATION NO. | : 11/565935 | |
| DATED | : April 20, 2010 | |
| INVENTOR(S) | : Koch et al. | |

It is certified that error appears in the above-identified patent and that said Letters Patent is hereby corrected as shown below:

Page 2,

Column 2 (Other Publications), Line 6, Before "Devices" insert -- Sensing --.

Column 13,

Line 14, Before "scattering" delete "30".

Column 14,

Line 44, In Claim 9, delete "anode" and insert -- mode --, therefor.

Line 45, In Claim 9, delete "herein" and insert -- wherein --, therefor.

Column 15,

Line 3, In Claim 13, delete "safe," and insert -- same --, therefor.

Line 9, In Claim 15, delete "pod" and insert -- port --, therefor.

Line 36, In Claim 24, after "wherein" insert -- a --.

Line 45, In Claim 27, after "through" delete "the".

Line 46, In Claim 27, delete "at" and insert -- of --, therefor.

Line 61, In Claim 28, delete "untied" and insert -- optical --, therefor.

Line 61, In Claim 28, delete "core, optical having an" and insert -- core --, therefor.

Line 65, In Claim 28, delete "core, having" and insert -- core --, therefor.

Signed and Sealed this
Fifteenth Day of February, 2011

David J. Kappos
*Director of the United States Patent and Trademark Office*

CERTIFICATE OF CORRECTION (continued)
U.S. Pat. No. 7,702,202 B2

Column 16,

Line 6, In Claim 28, delete "fiat" and insert -- first --, therefor.

Line 7, In Claim 28, delete "anodes," and insert -- modes, --, therefor.

Line 19, In Claim 30, delete "end" and insert -- and --, therefor.

Line 38, In Claim 33, delete "end" and insert -- and --, therefor.